United States Patent [19]

Böshagen et al.

[11] Patent Number: 4,774,240

[45] Date of Patent: Sep. 27, 1988

[54] N-INDOLYLETHYL-SULPHONIC ACID AMIDES AND THEIR USE

[75] Inventors: Horst Böshagen, Haan; Ulrich Rosentreter, Wuppertal; Folker Lieb, Leverkusen; Hermann Oediger, Cologne; Friedel Seuter; Elisabeth Perzborn, both of Wuppertal; Volker-Bernd Fiedler, Leverkusen, all of Fed. Rep. of Germany

[73] Assignee: Bayer Aktiengesellschaft, Leverkusen, Fed. Rep. of Germany

[21] Appl. No.: 852,475

[22] Filed: Apr. 14, 1986

[30] Foreign Application Priority Data

Apr. 24, 1985 [DE] Fed. Rep. of Germany ....... 3514696

[51] Int. Cl.[4] .................... A61K 31/40; C07D 209/14
[52] U.S. Cl. ................................ 514/228.2; 514/253; 514/254; 514/269; 514/274; 514/309; 514/312; 514/323; 514/339; 514/362; 514/363; 514/367; 514/369; 514/372; 514/381; 514/384; 514/394; 514/397; 514/418; 514/235.2; 544/58.5; 544/143; 544/316; 544/319; 544/373; 544/405; 546/141; 546/153; 546/157; 546/201; 546/273; 548/126; 548/136; 548/159; 548/186; 548/209; 548/213; 548/251; 548/255; 548/265; 548/327; 548/336; 548/507
[58] Field of Search ............... 548/507, 126, 136, 159, 548/186, 209, 213, 251, 255, 265, 327, 336; 514/418, 222, 229, 253, 254, 269, 271, 309, 312, 323, 339, 362, 363, 367, 369, 372, 381, 384, 397; 544/58.5, 143, 316, 319, 373, 405; 546/141, 153, 157, 201, 273

[56] References Cited

PUBLICATIONS

Journal of Pharmaceutical Sciences, Band 60, Nr. 4, Apr. 1971, Seiten 636–637; B. T. Ho et al.: "Hydroxyindole-O-methyltransferas e VI: Inhibitory Activities of Substituted benzoyltryptamines and benzenesulfonyltryptamines".

Journal of Medicinal Chemistry, Band 14, Nr. 6, Jun. 1971, Seiten 553–554; B. T. Ho et al.; "Central Nervous System Depressive Activity of Some Admides of Tryptamine" *Tabelle II, Berbindungen 10–13*.

Chemical Abstracts, Band 94, Nr. 19,11. May 1981, Seite 637, nr. 156681z, Columbus, Ohio, U.S.; D. R. Lagidze et al.: "Synthesis of Some New Analogs of Melatonin and Beta–Carboline from 4-Phenylpentanoic Acid", IZV. AKAD. NAUK GRUZ. SSR, SER. KHIM. *Zusammenfassung*.

Chemical Abstracts, Band 87, Nr. 19, 7. Nov. 1977, Seite 255, Nr, 148178f, Columbus, Ohio, U.S.; M. Wiechmann: "Scope and Limitations of the Analytical Use of Dansyl Chloride. I. The Reaction of Aromatic Sulfonyl Chlorides with Aliphatic Tertiary Amines: The Microanalytical Aspects of the Himsberg Test", Hoppe–SeylercS Z. Physiol. Chem. 1977, 358(8), 967–80 *Zusammenfassung*.

Journal of the Chemical Society, Perkin Transactions I, 1973, Seiten 1602–1606; A. S. Bailey et al.: "Further Examination of the Reactions of Simply Indoles with Arenesulphonyl Azides" *Seite 1605, Spalte 1, Absatz 2*.

Primary Examiner—Richard L. Raymond
Attorney, Agent, or Firm—Sprung Horn Kramer & Woods

[57] ABSTRACT

The invention relates to N-indolylethyl-sulphonic acid amides of the formula

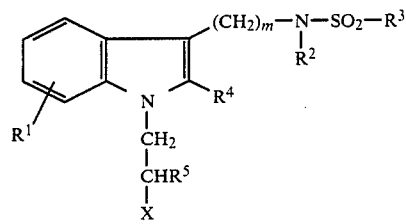

wherein $R^1$, $R^2$, $R^3$, $R^4$ and $R^5$ are defined in the specification and X is carboxyl, alkoxycarbonyl, cyano or carboxamido. These active compounds are useful in medicaments in combating thromboses, thromboembolisms, allergies or asthmatic disorders.

7 Claims, No Drawings

N-INDOLYLETHYL-SULPHONIC ACID AMIDES AND THEIR USE

The invention relates to new N-indolylethyl-sulphonic acid amides, processes for their preparation and their use as active compounds in medicaments.

New N-indolylethyl-sulphonic acid amides of the formula

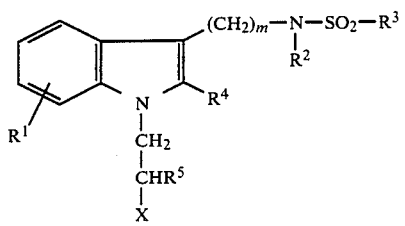

in which $R^1$ denotes hydrogen, halogen, trifluoromethyl, carboxyl, $C_1$ to $C_8$-alkoxycarbonyl, the group $$-S(O)_n-R^6$$

in which
$R^6$ denotes $C_1$ to $C_8$-alkyl or $C_6$ to $C_{12}$-aryl and
n denotes one of the numbers 0, 1 or 2, or denotes the group

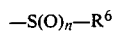

in which
$R^7$ and $R^8$ are identical or different and denote hydrogen, $C_1$ to $C_8$-alkyl, $C_6$ to $C_{12}$-aryl, $C_7$ to $C_{14}$-aralkyl or acetyl, or denotes the group $$-O-R^9$$

in which
$R^9$ denotes hydrogen, $C_1$ to $C_8$-alkyl, $C_6$ to $C_{12}$-aryl, $C_7$ to $C_{14}$-aralkyl, $C_1$ to $C_8$-$SO_2$-alkyl, $C_6$ to $C_{12}$-$SO_2$-aryl, $C_7$ to $C_{14}$-$SO_2$-aralkyl or trifluoromethyl,
or denotes $C_1$ to $C_8$-alkyl, $C_2$ to $C_8$-alkenyl or $C_5$ to $C_8$-cycloalkyl, optionally substituted by carboxyl, lower alkoxycarbonyl, halogen, hydroxyl, lower alkoxy and/or cyano,
$R^2$ denotes hydrogen, or denotes $C_1$ to $C_8$-alkyl or $C_2$ to $C_8$-alkenyl or $C_5$ to $C_8$-cycloalkyl, optionally substituted by halogen, carboxyl, lower alkoxycarbonyl, carboxamido and/or cyano,
$R^3$ denotes $C_1$ to $C_8$-alkyl, $C_2$ to $C_8$-alkenyl, $C_5$ to $C_8$-cycloalkyl, $C_6$ to $C_{12}$-aryl which is optionally substituted by halogen, cyano, trifluoromethyl, trifluoromethoxy, trifluoromethylthio, lower alkyl or lower alkenyl, which can themselves in turn be substituted by carboxyl or lower alkoxycarbonyl, lower alkoxy, hydroxyl, carboxyl, lower alkoxycarbonyl, phenyl, phenoxy, benzyloxy, benzylthio or the group

in which
$R^7$ and $R^8$ have the abovementioned meaning, or denotes saturated, unsaturated or aromatic optionally benzo-fused heterocyclyl which has 5 or 6 ring members, 1, 2 or 3 of which can be oxygen, sulphur and/or nitrogen, and is optionally substituted by lower alkyl, lower alkoxy, halogen, trifluoromethyl, trifluoromethoxy, amino, dimethylamino and/or acetylamino,
$R^4$ denotes hydrogen, $C_1$ to $C_8$-alkyl, $C_1$-$C_8$-hydroxyalkyl, $C_2$ to $C_8$-alkenyl, $C_5$-$C_8$-cycloalkyl, cyano, $C_6$ to $C_{12}$-aryl which is optionally substituted by halogen, methyl, methoxy or trifluoromethyl, $C_1$-$C_8$-alkylcarbonyl or saturated, unsaturated or aromatic heterocyclyl which has 5 or 6 ring members, 1, 2 or 3 of which can be oxygen, sulphur and/or nitrogen, and is optionally substituted by lower alkyl, lower alkoxy, lower alkoxycarbonyl, carboxyl, halogen, trifluoromethyl, trifluoromethoxy, amino, dimethylamino or acetylamino,
$R^5$ denotes hydrogen or $C_1$-$C_8$-alkyl,
X denotes carboxyl, $C_1$ to $C_8$-alkoxycarbonyl, cyano or carboxamido and
m denotes one of the numbers 2, 3 or 4,
and salts thereof, have been found.

According to the invention, the radical $R^1$ can have the following meaning:

A: hydrogen, halogen, hydroxyl, trifluoromethyl, carboxyl, $C_1$ to $C_8$-alkoxycarbonyl, the group $$-S(O)_n-R^6$$

in which
$R^6$ denotes $C_1$ to $C_8$-alkyl or $C_6$ to $C_{12}$-aryl and
n denotes one of the numbers 0, 1 or 2,
the group

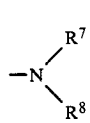

in which $R^7$ and $R^8$ are identical or different and denote hydrogen, $C_1$ to $C_8$-alkyl, $C_6$ to $C_{12}$-aryl, $C_7$ to $C_{14}$-aralkyl or acetyl, or the group $$-O-R^9$$

in which $R^9$ denotes hydrogn, $C_1$ to $C_8$-alkyl, $C_6$ to $C_{12}$-aryl, $C_7$ to $C_{14}$-aralkyl, $C_1$ to $C_8$-$SO_2$-alkyl, $C_6$ to $C_{12}$-$SO_2$-aryl, $C_7$ to $C_{14}$-$SO_2$-aralkyl or trifluoromethyl, or $C_1$ to $C_8$-alkyl, $C_2$ to $C_8$-alkenyl or $C_5$ to $C_8$-cycloalkyl, optionally substituted by carboxyl, lower alkoxycarbonyl, halogen, hydroxyl, lower alkoxy and/or cyano.

The preferred meaning of $R^1$ is

H: hydrogen, fluorine, chlorine, bromine, trifluoromethyl, carboxyl, lower alkoxycarbonyl, the group $$-S(O)_n-R^6$$

in which
$R^6$ denotes lower alkyl or phenyl and n denotes one of the numbers 0, 1 or 2,
the group

in which $R^7$ and $R^8$ are identical or different and denote hydrogen, lower akyl, phenyl, benzyl or acetyl, or the group

—O—$R^9$ in which $R^9$ denotes hydrogen, lower alkyl, phenyl, $C_7$ to $C_{10}$-aralkyl, —$SO_2$-lower alkyl, —$SO_2$-phenyl —$SO_2$-benzyl or trifluoromethyl, or lower alkyl, lower alkenyl, cyclopentyl or cyclohexyl, optionally substituted by identical or different substituents from the group comprising carboxyl, lower alkoxycarbonyl, fluorine, chlorine, bromine and/or cyano.

The particularly preferred meaning of $R^1$ is

O: hydrogen, fluorine, chlorine, bromine, trifluoromethyl, the group

in which
$R^6$ denotes methyl, ethyl or phenyl and
n denotes one of the numbers 0 or 2,
amino, methylamino, dimethylamino, acetylamino, the group

—O—$R^9$ in which $R^9$ denotes hydrogen, $C_1$ to $C_4$-alkyl, phenyl or benzyl, or $C_1$ to $C_4$-alkyl, optionally substituted by fluorine, chlorine and/or cyano.

Substitution of the radical $R^1$ in the 5-position of the indole system is especially preferred.

According to the invention, the radical $R^2$ can have the following meaning:

B: hydrogen, or $C_1$ to $C_8$-alkyl or $C_2$ to $C_8$-alkenyl or $C_5$ to $C_8$-cycloalkyl, optionally substituted by halogen, carboxyl, lower alkoxycarbonyl, carboxamido and/or cyano.

The preferred meaning of $R^2$ is

I: hydrogen, or lower alkyl, lower alkenyl, cyclopentyl or cyclohexyl, optionally substituted by fluorine, chlorine, bromine, carboxyl, lower alkoxycarbonyl and/or cyano.

The particularly preferred meaning of $R^2$ is

P: hydrogen, or $C_1$ to $C_4$-alkyl or $C_2$ to $C_4$-alkenyl, optionally substituted by carboxyl, $C_1$ to $C_4$-alkoxycarbonyl and/or cyano.

$R^2$ especially preferably has the meaning of V, which is hydrogen.

According to the invention, the radical $R^3$ can have the following meaning:

C: $C_1$ to $C_8$-alkyl, $C_2$ to $C_8$-alkenyl, $C_5$ to $C_8$-cycloalkyl, $C_6$ to $C_{12}$-aryl which is optionally substituted by halogen, cyano, trifluoromethyl, trifluoromethoxy, trifluoromethylthio, lower alkyl or lower alkenyl, which can themselves in turn be substituted by carboxyl or lower alkoxycarbonyl, lower alkoxy, hydroxyl, carboxyl, lower alkoxycarbonyl, phenyl, phenyloxy, benzyloxy, benzylthio or the group

in which $R^7$ and $R^8$ are identical or different and denote hydrogen, $C_1$ to $C_8$-alkyl, $C_6$ to $C_{12}$-aryl, $C_7$ to $C_{14}$-aralkyl or acetyl, or saturated, unsaturated or aromatic optionally benzo-fused heterocyclyl which has 5 or 6 ring members, 1, 2 or 3 of which can be oxygen, sulphur and/or nitrogen, and is optionally substituted by lower alkyl, lower alkoxy, halogen, trifluoromethyl, trifluoromethoxy, amino, dimethylamino and/or acetylamino.

The preferred meaning of $R^3$ is

J: lower alkyl, lower alkenyl, cyclopentyl or cyclohexyl, phenyl or naphthyl which is optionally substituted by up to four substituents from the group comprising fluorine, chlorine, bromine, cyano, hydroxyl, trifluoromethyl, trifluoromethoxy, lower alkyl, lower alkenyl, which can itself in turn be substituted by carboxyl or $C_1$ to $C_4$-alkoxycarbonyl, lower alkoxy, carboxyl, $C_1$- to $C_4$-alkoxycarbonyl, phenyl, phenoxy, benzyloxy, benzylthio and/or the group

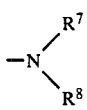

in which $R^7$ and $R^8$ are identical or different and denote hydrogen, lower alkyl, phenyl, benzyl or acetyl, or pyridyl, thienyl, furyl, pyrimidyl, piperazinyl, piperidyl, morpholinyl, thiomorpholinyl, quinolyl, isoquinolyl, imidazolyl, triazolyl, thiadiazolyl, pyrrolyl, benzimidazolyl, benzothiadiazolyl, indolyl, indolonyl, thiazolyl, isothiazolyl, benzothiazolyl, benzoisothiazolyl or benzoisothiazolonyl, optionally substituted by up to four subsitutents from the group comprising fluorine, chlorine, bromine, amino, dimethylamino, acetylamino, trifluoromethyl, trifluoromethoxy, $C_1$ to $C_4$-alkyl and/or $C_1$ to $C_4$-alkoxy.

The particularly preferred meaning of $R^3$ is

Q: $C_1$-$C_4$-alkyl, phenyl which is optionally substituted by up to three substituents from the group comprising fluorine, chlorine, bromine, cyano, hydroxyl, trifluoromethyl, $C_1$ to $C_4$-alkyl, carboxyvinyl, $C_1$ to $C_4$-alkoxy, $C_1$ to $C_4$-methor-ethoxycarbonylalkyl, amino, dimethylamino, acetylamino phenyl and/or phenoxy, naphthyl, or pyridyl, thienyl, furyl, pyrimidyl, piperazinyl, piperidinyl, morpholinyl, quinolyl, benzothiadiazolyl, benzoisothiazolonyl or indolonyl, substituted by $C_1$-$C_4$-alkyl, fluorine, chlorine, amino or dimethylamino.

According to the invention, the radical $R^4$ can have the following meaning:

D: hydrogen, $C_1$ to $C_8$-alkyl, $C_1$ to $C_8$-hydroxyalkyl, $C_2$ to $C_8$-alkenyl, cyano, $C_6$ to $C_{12}$-aryl which is optionally substituted by halogen, methyl, methoxy or trifluoromethyl, $C_1$-$C_8$-alkylcarbonyl, or saturated, unsaturated or aromatic heterocyclyl which has 5 or 6 ring members, 1, 2 or 3 of which can be oxygen, sulphur and/or nitrogen, optionally substituted by lower alkyl, lower alkoxy, lower alkoxycarbonyl, carboxyl, halogen, trifluoromethyl, trifluoromethoxy, amino, dimethylamino or acetylamino.

The preferred meaning of $R^4$ is

K: hydrogen, lower alkyl, lower alkenyl, lower hydroxyalkyl, cyano, lower alkylcarbonyl or phenyl, pyridyl, thienyl, furyl, pyrimidyl, imidazolyl or pyrrolyl optionally substituted by up to three substituents from the group comprising fluorine, chlorine, methyl, methoxy and/or trifluoromethyl.

The particularly preferred meaning of $R^4$ is

R: hydrogen, methyl, ethyl, methylcarbonyl, cyano, hydroxymethyl, hydroxyethyl or phenyl.

According to the invention, $R^5$ can have the following meaning:

E: $C_1$-$C_8$-alkyl or hydrogen.

The preferred meaning of $R^5$ is

L: lower alkyl or hydrogen.

The particularly preferred meaning of $R^5$ is

S: $C_1$-$C_4$-alkyl or hydrogen.

According to the invention, the radical X can have the following meaning:

F: carboxyl, $C_1$ to $C_8$-alkoxycarbonyl, cyano or carboxamido.

The preferred meaning of X is

M: carboxyl, lower alkoxycarbonyl or cyano.

The particularly preferred meaning of X is

T: carboxyl, $C_1$ to $C_4$-alkoxycarbonyl or cyano.

X especially preferably denotes W, which is carboxyl.

According to the invention, the index m can have the following meaning:

G: one of the numbers 2, 3 or 4.

The preferred meaning of m is

N: one of the numbers 2 or 3.

The particularly preferred meaning of m is U, which is 2.

In the context of the present invention, N-indolyl-ethylsulphonic acid amides in which the substitutents $R^1$, $R^2$, $R^3$, $R^4$, $R^5$ and x and the index m are linked in the following manner are preferred:

| $R^1$ | $R^2$ | $R^3$ | $R^4$ | $R^5$ | X | m |
| --- | --- | --- | --- | --- | --- | --- |
| A | B | C | D | L | F | G |
| O | P | Q | R | L | T | U |
| A | B | C | D | E | M | G |
| O | P | Q | R | S | M | U |
| A | B | C | D | E | F | N |
| O | P | Q | R | S | T | N |
| O | B | C | D | E | F | G |
| O | I | J | K | L | M | N |
| A | P | C | D | E | F | G |
| H | P | J | K | L | M | N |
| A | B | Q | D | E | F | G |
| H | I | Q | K | L | M | N |
| A | B | C | R | E | F | G |
| H | I | J | R | L | M | N |
| A | B | C | D | S | F | G |
| H | I | J | K | S | M | N |
| A | B | C | D | E | T | G |
| H | I | J | K | L | T | N |
| A | B | C | D | E | F | U |
| H | I | J | K | L | M | U |
| A | V | C | D | E | F | G |
| H | V | J | K | L | M | N |
| O | V | Q | R | S | T | U |
| A | B | C | D | E | W | G |
| H | I | J | K | L | W | N |
| O | P | Q | R | S | W | U |
| A | V | C | D | E | W | G |
| H | V | J | K | L | W | N |
| O | V | Q | R | S | W | U |
| A | B | C | D | E | F | G |
| H | I | J | K | L | M | N |
| O | P | Q | R | S | T | U |
| A | I | J | K | L | M | N |

| $R^1$ | $R^2$ | $R^3$ | $R^4$ | $R^5$ | X | m |
| --- | --- | --- | --- | --- | --- | --- |
| A | P | Q | R | S | T | U |
| H | B | J | K | L | M | N |
| O | B | Q | R | S | T | U |
| H | I | C | K | L | M | N |
| O | P | C | R | S | T | U |
| H | I | J | D | L | M | N |
| O | P | Q | D | S | T | U |
| H | I | J | K | E | M | N |
| O | P | Q | R | E | T | U |
| H | I | J | K | L | F | N |
| O | P | Q | R | S | F | U |
| H | I | J | K | L | M | G |
| O | P | Q | R | S | T | G |
| H | B | J | K | L | M | N |
| H | P | Q | K | L | M | N |
| A | I | C | D | E | F | G |
| O | I | Q | R | S | T | U |
| H | B | C | D | E | F | G |
| H | P | Q | R | S | T | U |
| A | B | J | D | E | F | G |
| O | P | J | R | S | T | U |
| A | B | C | K | E | F | G |
| O | P | Q | K | S | T | U |

N-Indolylethyl-sulphonic acid amides with the linkages H, I, J, K, L, M, N and O, P, Q, R, S, T, U are particularly preferred.

Particularly preferred are as well N-dindolylethyl-sulphonic acid amids with $R^1$ denoting fluorine, $R^2$ hydrogen, $R^3$ phenyl substituted with fluorine, $R^4$ and $R^6$ hydrogen and X—COOH.

According to the invention, alkyl in general represents a straight-chain or branched hydrocarbon radical with 1 to 8 carbon atoms. Lower alkyl with 1 to about 6 carbon atoms is preferred. An alkyl radical with 1 to 4 carbon atoms is particularly preferred. The following alkyl radicals may be mentioned as examples: methyl, ethyl, propyl, isopropyl, butyl, isobutyl, pentyl, isopentyl, hexyl, isohexyl, heptyl, isoheptyl, octyl and isooctyl.

Alkenyl in general represents a straight-chain or branched hydrocarbon radical with 2 to 8 carbon atoms and one or more, preferably one or two, double bonds. The lower alkenyl radical with 2 to about 6 carbon atoms and one double bond is preferred. An alkenyl radical with 2 to 4 carbon atoms and one double bond is particularly preferred. The following alkenyl radicals may be mentioned as examples: vinyl, allyl, propenyl, isopropenyl, butenyl, isobutenyl, pentenyl, isopentenyl, hexenyl, isohexenyl, heptenyl, isoheptenyl, octenyl and isooctenyl.

According to the invention, alkoxy in general represents a straight-chain or branched hydrocarbon chain which has 1 to 8 carbon atoms and is bonded via oxygen. Lower alkoxy with 1 to about 6 carbon atoms is preferred. An alkoxy radical with 1 to 4 carbon atoms is particularly preferred. The following alkoxy radicals may be mentioned as examples: methoxy, ethoxy, propoxy, isopropoxy, butoxy, isobutoxy, pentoxy, isopentoxy, hexoxy, isohexoxy, heptoxy, isoheptoxy, octoxy and isooctoxy.

According to the invention, cycloalkyl in general represents a cyclic hydrocarbon radical with 5 to 8 carbon atoms. The cyclopentane and cyclohexane radical is preferred. The following cycloalkyl radicals may be mentioned as examples: cyclopentyl, cyclohexyl, cycloheptyl and cyclooctyl.

According to the invention, aryl in general represents an aromatic radical with 6 to 12 carbon atoms. Preferred aryl radicals are phenyl, naphthyl and biphenyl.

According to the invention, aralkyl in general represents an aryl radical which has 7 to 14 carbon atoms and is bonded via an alkylene chain. Aralkyl radicals with 1 to 6 carbon atoms in the aliphatic part and 6 to 12 carbon atoms in the aromatic part are preferred. The following aralkyl radicals may be mentioned as examples: benzyl, naphthylmethyl and phenethyl.

Alkoxycarbonyl can be represented, for example, by the formula

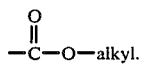

In this formula, alkyl represents a straight-chain or branched hydrocarbon radical with 1 to 8 carbon atoms. Lower alkoxycarbonyl with 1 to about 6 carbon atoms in the alkyl part is preferred. An alkoxycarbonyl radical with 1 to 4 carbon atoms in the alkyl part is particularly preferred. The following lower alkoxycarbonyl radicals may be mentioned as examples: methoxycarbonyl, ethoxycarbonyl, propoxycarbonyl, isopropoxycarbonyl, butoxycarbonyl and isobutoxycarbonyl.

According to the invention, halogen in general represents fluorine, chlorine, bromine or iodine, preferably fluorine, chlorine or bromine and particularly preferably fluorine or chlorine.

The radicals $R^1$, $R^2$, $R^3$, $R^4$ and X can optionally be substituted by other radicals. Substitution of up to 4 other radicals, particularly preferably by up to 3 other radicals and especially preferably by up to 2 other radicals are preferred.

The N-indolylethyl-sulphonic acid amides according to the invention can also be in the form of their salts. In general salts with organic or inorganic bases may be mentioned here.

Physiologically acceptable salts are preferred in the context of the present invention. Physiologically acceptable salts of the N-indolylethyl-sulphonic acid amides can be metal or ammonium salts of the substances according to the invention which have a free carboxyl group. Particularly preferred salts are, for example, sodium, potassium, magnesium or calcium salts and ammonium salts which are derived from ammonia or organic amines, such as, for example, ethylamine, di- or triethylamine, di- or triethanolamine, dicyclohexylamine, dimethylaminoethanol, arginine or ethylenediamine.

The following N-indolylethyl-sulphonic acid amides may be mentioned as examples: N-[2-[1-(2-carboxyethyl)-1H-indol-3-yl]]ethyl-(4-methyl-phenyl)sulphonamide, N-[2-[1-(2-carboxyethyl)-5-methoxy-1H-indol-3-yl]]ethyl-phenylsulphonamide sodium salt, N-[2-[1-(2-carboxyethyl)-5-hydroxy-1H-indol-3-yl]]ethyl-phenylsulphonamide sodium salt, N-[2-[5-benzyloxy-1-(2-carboxyethyl)-1H-indol-3-yl]]ethyl-phenyl-sulphonamide, N-[2-[1-(2-carboxyethyl)-1-H-indol-3-yl]]ethyl-(4-chlorophenyl)sulphonamide triethylamine salt, N-[2-[1-(2-carboxyethyl)-1H-indol-3-yl]]ethyl-(2,5-dichlorophenyl)sulphonamide, N-[2-[1-(2-carboxyethyl)-2-methyl-1H-indol-3-yl]]ethyl-phenylsulphonamide, N-[2-[1-(2-carboxyethyl)-1H-indol-3-yl]]ethyl-(2,4-dichlorophenyl)-sulphonamide, N-[2-[1-(2-carboxyethyl)-1H-indol-3-yl]]ethyl-2-thienylsulphonamide, N-[2-[1-(2-carboxyethyl)-5-methyl-1H-indol-3-yl]]ethyl-phenylsulphonamide, N-[2-[1-(2-carboxyethyl)-1H-indol-3-yl]]ethyl-(4-phenoxyphenyl)sulphonamide and N-[2-[1-(2-carboxyethyl)-1H-indol-3-yl]]ethyl-3-pyridylsulphonamide.

The invention also relates to a process for the preparation of N-indolylethyl-sulphonic acid amides or salts thereof, which is characterised in that indolyl-alkylamines of the formula

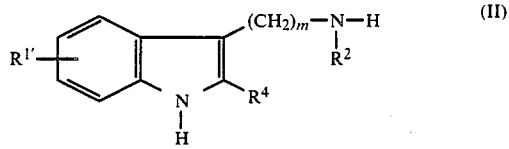

in which $R^{1'}$ denotes hydrogen, halogen, trifluoromethyl, carboxyl, $C_1$ to $C_8$-alkoxycarbonyl, the group

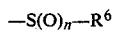

in which $R^6$ denotes $C_1$ to $C_8$-alkyl or $C_6$ to $C_{12}$-aryl and n denotes one of the numbers 0, 1 or 2, or denotes the group

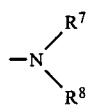

in which $R^7$ and $R^8$ are identical or different and denote hydrogen, $C_1$ to $C_8$-alkyl, $C_6$ to $C_{12}$-aryl, $C_7$ to $C_{14}$-aralkyl or acetyl, or denotes the group

in which $R^9$ denotes $C_1$ to $C_8$-alkyl, $C_6$ to $C_{12}$-aryl, $C_7$ to $C_{14}$-aralkyl, $C_1$ to $C_8$-$SO_2$-alkyl, $C_6$ to $C_{12}$-$SO_2$-aryl, $C_7$ to $C_{14}$-$SO_2$-aralkyl or trifluoromethyl, or denotes $C_1$ to $C_8$-alkyl, $C_2$ to $C_8$-alkenyl or $C_5$ to $C_8$-cycloalkyl, optionally substituted by carboxyl, lower alkoxycarbonyl, halogen, hydroxyl, lower alkoxy and/or cyano, $R^2$ denotes hydrogen, or denotes $C_1$ to $C_8$-alkyl or $C_2$ to $C_8$-alkenyl or $C_5$ to $C_8$-cycloalkyl, optionally substituted by halogen, carboxyl, lower alkoxycarbonyl, carboxamido and/or cyano, Rhu 4 denotes hydrogen, $C_1$ to $C_8$-alkyl, $C_1$–$C_8$-hydroxyalkyl, $C_2$ to $C_8$-alkenyl, $C_5$–$C_8$-cycloalkyl, $C_1$–$C_8$-alkylcarbonyl, cyano, $C_6$ to $C_{12}$-aryl which is optionally substituted by halogen, methyl, methoxy or trifluoromethyl, or saturated, unsaturated or aromatic heterocyclyl which has 5 or 6 ring members, 1, 2 or 3 or which can be oxygen, sulphur and/or nitrogen, and is optionally substituted by lower alkyl, lower alkoxy, lower alkoxycarbonyl, carboxyl, halogen, trifluoromethyl, trifluoromethoxy, amino, dimethylamino or acetylamino and m denotes one of the numbers 2, 3 or 4, are reacted with sulphonic acid halides of the formula $$R^3-SO_2-Y \qquad (III)$$

in which R³ denotes C₁ to C₈-alkyl, C₂ to C₈-alkenyl, C₅ to C₈-cycloalkyl, C₆ to C₁₂-aryl which is optionally substituted by halogen, cyano, hydroxyl, trifluoromethyl, trifluoromethoxy, trifluoromethylthio, lower alkyl or lower alkenyl, which can themselves in turn be substituted by carboxyl or lower alkoxycarbonyl, lower alkoxy, carboxyl, lower alkoxycarbonyl, phenyl, phenoxy, benzyloxy, benzylthio or the group

in which
R⁷ and R⁸ have the abovementioned meaning, or saturated, unsaturated or aromatic optionally fused heterocyclyl which has 5 or 6 ring members, 1, 2 or 3 of which can be oxygen, sulphur and/or nitrogen, and is optionally substituted by lower alkyl, lower alkoxy, halogen, trifluoromethyl, trifluoromethoxy, amino, dimethylamino and/or acetylamino and
Y represents halogen,
in the presence of an inert solvent, if appropriate in the presence of a base, and the product is then alkylated with an olefinic compound of the formula $$CH_2=C-X' \quad (IV)$$
$$\quad \quad | $$
$$\quad \quad R^5$$

in which
X' denotes C₁ to C₈-alkoxycarbonyl, cyano or carboxamido and
R⁵ denotes hydrogen or C₁-C₈-alkyl,
in the presence of an inert solvent, if appropriate in the presence of a base, and, in the case of preparation of compounds substituted by hydroxyl in the 4-, 5-, 6- or 7-position the corresponding benzyloxy compounds are then hydrogenated in the presence of a catalyst in an inert solvent, if appropriate in the presence of an acid, and, in the case of the preparation of N-indolylethylcarboxyl compounds, the corresponding nitriles or alkoxycarbonyl are then hydrolyzed, and, in the case of preparation of salts, the products are then reacted with a corresponding base.

The process according to the invention can be illustrated, for example, by the following equation:

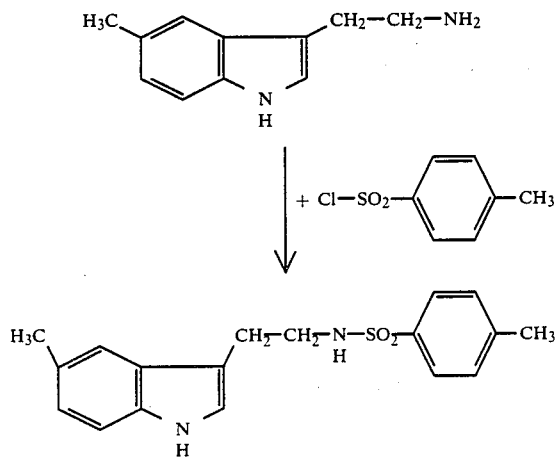

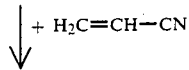

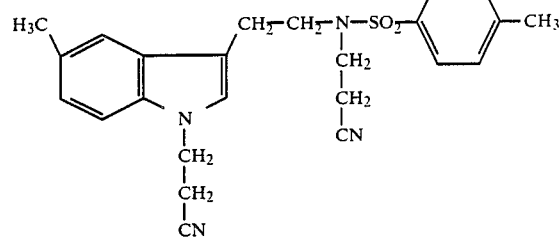

Hydrolysis

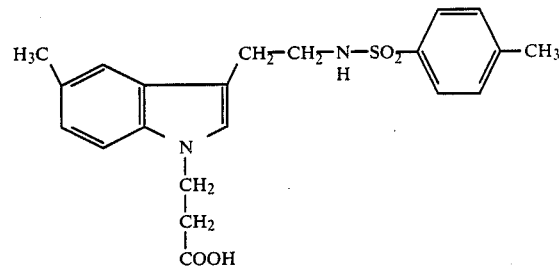

Intermediates are in general formed in carrying out the process according to the invention and can be isolated. Thus, it is possible to carry out the process according to the invention in several process stages. However, it may also be possible to combine various process steps and to carry them out as a one-pot process.

The indolylalkylamines (formula II), the sulphonic acid halides (formula III) and the olefinic compounds (formula IV) are known per se or can be prepared by methods which are known per se (Houben-Weyl, Methoden der organischen Chemie (Methods of Organic Chemistry), Volume 9, 407 et seq. and 547 et seq. (1959); The Chemistry of Indoles, Academic Press (1970); W. J. Houlihan, Indoles Part Two, John Wiley and Sons (1972)).

Solents for the process according to the invention can be inert organic solvents which do not change under the reaction conditions. These include, preferably, alcohols, such as, for example, methanol, ethanol, n-propanol and isopropanol, ethers, such as, for example, diethyl ether, dioxane and tetrahydrofuran, halogenohydrocarbons, such as methylene chloride, chloroform or carbon tetrachloride, dichloroethylene and trichloroethylene, ethyl acetate, toluene, acetonitrile, nitromethane, dimethylformamide, hexamethylphosphoric acid triamide, pyridine and acetone. It is of course possible to employ mixtures of the solvents.

Possible bases for the process according to the invention are the customary basic compounds for basic reactions. These include, preferably, alkali metal and alkaline earth metal hydroxides or carbonates, such as, for example, lithium, sodium, potassium, calcium or barium hydroxide and sodium or potassium carbonate, alkali metal alcoholates, such as sodium methylate and ethylate or potassium methylate and ethylate, or organic bases, such as, for example, triethylamine, pyridine or 1-methylpiperidine, benzyltrimethylammonium hydroxide or tetrabutylammonium hydroxide.

The process according to the invention is in general carried out in the temperature range from −20° to +100° C., preferably from 0° C. to 80° C.

The process according to the invention is in general carried out under normal pressure. However, it is also possible to carry out the process under reduced or increased pressure (for example in the pressure range from 1 to 10 bar.

In general, 1 to 5 moles, preferably 1 to 2 moles and particularly preferably 1 mole, of sulphonic acid halide are employed per mole of the indolylalkylamine. The olefinic compound is in general employed in an amount of 1 to 10 moles, preferably 1 to 5 moles and particularly preferably 3 moles, per mole of the indolylalkylamine. In the preparation of N-indolylethyl-sulphonic acid amides which are substituted by hydroxyl in the 4-, 5-, 6- or 7-position the corresponding benzyloxy compound is hydrogenated in the presence of a catalyst and an inert organic solvent, if appropriate in the presence of an acid.

Solvents which may be mentioned are inert organic solvents which do not change under the hydrogenation conditions. These include, preferably, alcohols, such as methanol, ethanol, propanol or iso-propanol, ethers, such as diethyl ether, dioxane or tetrahydrofuran, chlorohydrocarbons, such as methylene chloride, chloroform or carbon tetrachloride or 1,2-dichloroethane, toluene or ethyl acetate.

The hydrogenation is preferably carried out in the presence of noble metal catalysts. Platinum, palladium or palladium/animal charcoal catalysts are particularly preferred. The catalyst is in general employed in an amount of 1 to 100 mol %, preferably 5 to 10 mol %, based on the benzyloxyindolyl compound.

Acids which can be employed according to the invention are strong mineral acids, but also organic acids. Hydrogen halide acids, such as hydrochloric or hydrobromic acid, sulphuric acid, phosphoric acid, perchloric acid, acetic acid and trifluoroacetic acid are preferred. In general, 1 to 100 parts by weight, preferably 1 to 50 parts by weight, of acid are employed, based on the benzyloxy compound.

The hydrogenation is in general carried out in the temperature range from −20° to +100° C., preferably in the range from 0° to 50° C.

The hydrogenation is in general carried out under normal pressure. However, it can also be carried out under increased or reduced pressure (for example in the pressure range from 0.5 to 50 bar).

In the case of preparation of N-indolyl-ethylcarboxyl compounds, corresponding nitriles or alkoxycarbonyl compounds are hydrolyzed. The hydrolysis is in general carried out in the presence of bases, preferably alkali metal or alkaline earth metal hydroxides or alcoholates. Bases such as alkali metal or alkaline earth metal hydroxides or alkali metal alcoholates, preferably lithium, sodium, potassium, calcium or barium hydroxide or sodium or potassium methylate or ethylate, are preferably used.

In general, 1 to 100 moles, preferably 2 to 50 moles, of the base are employed per mole of the nitrile or alkoxycarbonyl compound.

Examples which may be mentioned of indolylalkylamines for the process according to the invention are: 2-(5-methyl-1H-indol-3-yl)ethylamine, 2-(2-methyl-1H-indol-3-yl)ethylamine, 2-(5-methoxy-1H-indol-3-yl)ethylamine, 2-(5-benzyloxy-1H-indol-3-yl)ethylamine, tryptamihe, 2-(2-isopropyl-1H-indol-3-yl)ethylamine and 2-(2-tert.-butyl-H-indol-3-yl)ethylamine.

Examples which may be mentioned of sulphonic acid halides for the process according to the invention are: 4-toluenesulphonyl chloride, 4-chlorophenylsulphonyl chloride, 2,5-dichlorophenylsulphonyl chloride, 3-trifluoromethylphenylsulphonyl chloride, 2,4-dichlorophenylsulphonyl chloride, 4-methoxyphenylsulphonyl chloride, 1-naphthylsulphonyl chloride, 2,4,6-trimethylphenylsulphonyl chloride, quinolyl-8-sulphonyl chloride, thienyl-2-sulphonyl chloride, 2,6-dichlorophenylsulphonyl chloride and 2,3,4-trichlorophenylsulphonyl chloride.

Examples which may be mentioned of olefinic compounds for the process according to the invention are: acrylonitrile, methyl acrylate, ethyl acrylate and methacrylonitrile.

The process according to the invention can be carried out, for example, as follows: the indolylalkylamine is dissolved and the sulphonic acid halide is added dropwise. The intermediate product formed in the reaction can be isolated.

The reaction of the intermediate product with the olefinic compound is carried out at room temperature, with stirring. Working up is carried out in a manner which is known per se.

N-Indolylethyl-sulphonic acid amides of high purity are obtained in high yields by the process according to the invention.

The new N-indolylethyl-sulphonic acid amides and salts thereof can be used as active compounds in medicaments. The active compounds have a platelet aggregation-inhibiting and thromboxan-antagonistic action. They can preferably be employed for the treatment of thromboses, thromboembolisms and ischaemias, as antiasthmatics and as antiallergics. The new active compounds can be converted into the customary formulations, such as tablets, capsules, dragees, pills, granules, aerosols, syrups, emulsions, suspensions and solutions, in a manner which is known per se using inert nontoxic pharmaceutically suitable excipients or solvents. The therapeutically active compound should in each case be present here in the total mixture in a concentration of about 0.5 to 90% by weight, preferably 10 to 70% by weight, that is to say in amounts which are sufficient to achieve the stated dosage range.

The formulations are prepared, for example, by extending the active compounds with solvents and/or excipients, if appropriate using emulsifying agents and/or dispersing agents, and, for example, in the case where water is used as the diluent, organic solvents can be used, if appropriate, as auxiliary solvents.

Examples of auxiliary substances which may be mentioned are: water, non-toxic organic solvents, such as paraffins (for example petroleum fractions), vegetable oils (for example groundnut/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silicic acid and silicates) and sugars (for example sucrose, lactose and glucose), emulsifying agents (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration can be effected in the customary manner, preferably orally or parenterally, in particular perlingually or intravenously. In the case of oral use, tablets can of course also contain, in addition to the excipients mentioned, additives, such as sodium citrate, calcium carbonate and dicalcium phosphate, together with various adjuvants, such as starch, preferably potato starch, gelatine and the like. Lubricants, such as magnesium stearate, sodium lauryl-sulphate and talc, can furthermore be co-used for tablet-making. In the case of aqueous suspensions and/or elixirs intended for oral use, various flavor-improving agents or colorants can be added to the active compounds, in addition to the abovementioned auxiliary substances.

In the case of parenteral use, solutions of the active compounds can be employed, using suitable liquid excipients.

In general, it has proved advantageous, in the case of intravenous administration, to administer amounts of about 0.001 to 1 mg/kg, preferably about 0.01 to 0.5 mg/kg of body weight, in order to achieve effective results. In the case of oral administration, the dosage is in general about 0.01 to 20 mg/kg, preferably 0.1 to 10 mg/kg of body weight.

Nevertheless, it may at times be necessary to deviate from the amounts mentioned, and in particular to do so as a function of the body weight or the nature of the administration route, the individual behaviour towards the medicament, the nature of its formulation and the time or interval at which administration takes place. Thus, in some cases it can suffice to manage with less than the above-mentioned minimum amount, whilst in other cases the upper limit mentioned must be exceeded. Where relatively large amounts are administered, it may be advisable to distribute these into several individual doses over the day.

The N-indolylethyl-sulphonic acid amides according to the invention can be used both in human medicine and in veterinary medicine.

PREPARATION EXAMPLES

Example 1

N-[2-[1-(2-Carboxyethyl)-1H-indol-3-yl]]ethyl-(4-methylphenyl)sulphonamide

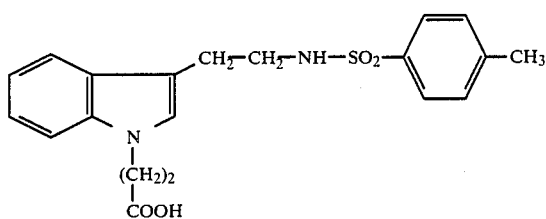

(a) N-[2-(1H-Indol-3-yl)]ethyl-(4-methylphenyl)sulphonamide

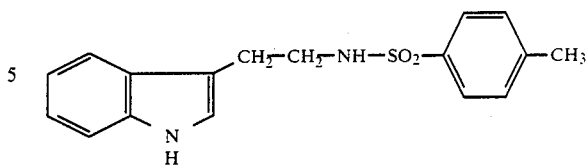

17.5 g (110 mmol) of tryptamine and 18.0 g (220 mmol) of sodium acetate are dissolved in 250 ml of ethanol. 20.97 g (110 mmol) of p-toluenesulphonyl chloride, dissolved in 100 ml of ethanol, are added dropwise at 0° C. The mixture is stirred first at room temperature for 1 hour and then under reflux for 1 hour. Water is then added in an amount such that a clear solution forms. Some of the ethanol is distilled off. The product crystallizes out and is filtered off with suction and recrystallized from isopropanol.

Yield: 20.7 g (60% of theory)
Melting point: 118° C.
Rf value 0.6 in toluene:ethanol=3:1

(b) N-[2-Cyanoethyl]-N-[2-[1-(2-cyanoethyl)-1H-indol-3-yl]]ethyl-(4-methylphenyl)sulphonamide

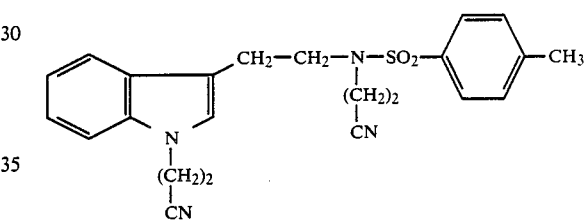

10 g of 1(a) are dissolved in 150 ml of dioxane. 10 ml of acrylonitrile are then added. 1 ml of benzyltrimethylammonium hydroxide solution (40% strength), dissolved in 4 ml of methanol, is added to this solution. The mixture is stirred at room temperature for 5 hours and then poured into water. It is extracted three times with ethyl acetate. The organic phase is washed with water, dried over MgSO$_4$ and filtered with suction and the filtrate is concentrated in a rotary evaporator. The product crystallizes out with a little ether. It is recrystallized from ethanol/acetonitrile (1:1).

Yield: 10.1 g (75.5% of theory)
Meltig point: 88° C.
Rf value 0.5 in toluene:ethanol=3:1

(c) N-[2-[1-(2-Carboxyethyl)-1H-indol-3-yl]]ethyl-(4-methypheny)sulphonamide 10 g of 1(b) are stirred in 300 ml of 10% strength potassium hydroxide solution under reflux for 3 hours. The mixture is then rendered acid with 6 molar HCl and extracted three times with chloroform. The organic phase is washed twice with water, dried over MgSO$_4$ and concentrated on a rotary evaporator. The product crystallizes out with a little ethyl acetate and is filtered off with suction.

Yield: 4.7 g (51.1% of theory)
Melting point: 126° C.

Example 2

N-[2-[1-(2-Carboxyethyl)-5-methoxy-1H-indol-3-yl]]ethyl-phenylsulphonamide sodium salt

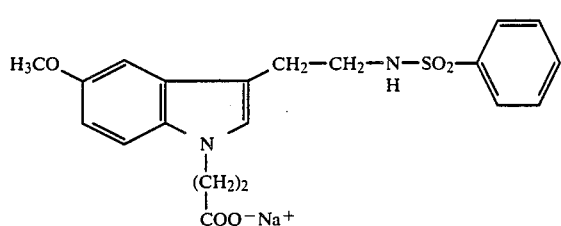

9.4 g of N-[2-[1-(2-carboxyethyl)-5-methoxy-1H-indol-3-yl]]ethyl-phenylsulphonamide (prepared analogously to Example 1) are dissolved in 200 ml of methanol and 1.26 g of sodium methylate are added. The methanol is then stripped off on a rotary evaporator and the solid residue is stirred with ether.

Yield: 7.85 g (77% of theory)

Melting point: 225° C.

Rf value 0.51 in $CH_2Cl$:methanol = 9:1

Example 3

N-[2-[1-(2-Carboxyethyl)-5-hydroxy-1H-indol-3-yl]]ethyl-phenylsulphonamide sodium salt

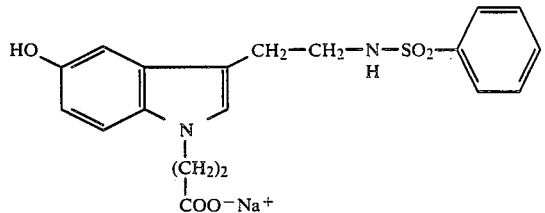

3 g of N-[2-[5-benzyloxy-1-(2-carboxyethyl)-1H-indol-3-yl]]ethyl-phenylsulphonamide (prepared analogously to Example 1) are dissolved in a mixture of 50 ml of ethanol and 15 ml of ethyl acetate, and 200 mg of 10% strength palladium on active charcoal are added. Hydrogenation is carried out under normal pressure until the uptake of hydrogen has ended. The catalyst is then filtered off, the filtrate is evaporated and the residue is dissolved in methylene chloride. The methylene chloride solution is extracted twice with saturated bicarbonate solution and the combined bicarbonate phases are rendered acid with 1 molar sulphuric acid and extracted with ethyl acetate. The ethyl acetate phase is dried over $MgSO_4$ and evaporated. 1.5 g of oil, which is converted into the sodium salt of the free acid analogously to Example 2, are thus obtained.

Yield: 1.76 g (62.4% of theory).

Melting point: 100° C. (decomposition).

Examples 4 to 19

The compounds listed in the following table were prepared in accordance with the working instructions of Example 1:

Structural formula (header):

$R^1$-substituted indole with N-substituent: $-CH_2-CH_2-N(R^2)-SO_2-R^3$ and $R^4$ at position 3.

| Example No. | $R^1$ | $R^2$ | $R^3$ | $R^4$ | Z | Melting point (°C.) | Rf value in |
|---|---|---|---|---|---|---|---|
| 4a | H | $CH_2CH_2CN$ | 4-Cl—$C_6H_4$ | H | $CH_2CH_2CN$ | 103 | 0.41 Toluene:Ethanol = 3:1 |
| b | H | H | 4-Cl—$C_6H_4$ | H | $CH_2CH_2COOH \cdot NEt_3$ | 97 | 0.34 Toluene:Ethanol = 3:1 |
| 5a | H | $CH_2CH_2CN$ | $C_6H_5$ | H | $CH_2CH_2CN$ | 122 | 0.47 Toluene:Ethanol = 3:1 |
| b | H | H | $C_6H_5$ | H | $CH_2CH_2COOH \cdot NEt_3$ | 108 | 0.34 $CHCl_3$:Methanol = 10:1 |
| 6a | H | $CH_2CH_2CN$ | 2,5-Di-Cl—$C_6H_3$ | H | $CH_2CH_2CN$ | 152 | 0.53 Toluene:Ethanol = 3:1 |
| b | H | H | 2,5-Di-Cl—$C_6H_3$ | H | $CH_2CH_2COOH$ | Oil | 0.47 Toluene:Ethanol = 3:1 |
| c | H | H | 2,5-Di-Cl—$C_6H_3$ | $CH_3$ | H | 132 | 0.42 Toluene:Ethanol = 3:1 |
| 7a | H | $CH_2CH_2CN$ | $C_6H_5$ | $CH_3$ | $CH_2CH_2CN$ | 136 | 0.5 Toluene:Ethanol = 3:1 |
| b | H | H | $C_6H_5$ | $CH_3$ | $CH_2CH_2COOH \cdot NEt_3$ | 145 | 0.49 Toluene:Ethanol = 3:1 |
| c | H | H | $C_6H_5$ | $CH_3$ | H | 127 | 0.22 $CHCl_3$:Methanol = 10:1 |
| 8a | H | $CH_2CH_2CN$ | 3-$F_3C$—$C_6H_4$ | H | $CH_2CH_2CN$ | 104 | 0.52 Toluene:Ethanol = 3:1 |
| b | H | H | 3-$F_3C$—$C_6H_4$ | H | $CH_2CH_2COOH$ | 133 | 0.51 Toluene:Ethanol = 3:1 |
| c | H | H | 3-$F_3C$—$C_6H_4$ | H | H | 138 | 0.39 Toluene:Ethanol = 3:1 |
| 9a | H | $CH_2CH_2CN$ | 2,4,6-Tri-$H_3C$—$C_6H_2$ | H | $CH_2CH_2CN$ | 139 | 0.55 Toluene:Ethanol = 3:1 |
| b | H | H | 2,4,6-Tri-$H_3C$—$C_6H_2$ | H | $CH_2CH_2COOH$ | Oil | 0.51 Toluene:Ethanol = 3:1 |
| c | H | H | 2,4,6-Tri-$H_3C$—$C_6H_2$ | H | H | 139 | 0.49 Toluene:Ethanol = 3:1 |
| 10a | H | $CH_2CH_2CN$ | 1-Piperidyl | H | $CH_2CH_2CN$ | 98 | 0.46 Toluene:Ethanol = 3:1 |
| b | H | H | 1-Piperidyl | H | $CH_2CH_2COOH$ | Oil | 0.42 Toluene:Ethanol = 3:1 |
| c | H | H | 1-Piperidyl | H | H | Oil | 0.5 Toluene:Ethanol = 3:1 |
| 11a | H | $CH_2CH_2CN$ | 2,4-Di-Cl—$C_6H_3$ | H | $CH_2CH_2CN$ | 55 | 0.48 Toluene:Ethanol = 3:1 |
| b | H | H | 2,4-Di-Cl—$C_6H_3$ | H | $CH_2CH_2COOH$ | 131 | 0.6 Toluene:Ethanol = 3:1 |
| c | H | H | 2,4-Di-Cl—$C_6H_3$ | H | H | 89–95 | 0.32 Toluene:Ethanol = 3:1 |
| 12a | H | $CH_2CH_2CN$ | 4-$H_3CO$—$C_6H_4$ | H | $CH_2CH_2CN$ | 115 | 0.45 Toluene:Ethanol = 3:1 |
| b | H | H | 4-$H_3CO$—$C_6H_4$ | H | $CH_2CH_2COOH$ | Oil | 0.56 Toluene:Ethanol = 3:1 |
| c | H | H | 4-$H_3CO$—$C_6H_4$ | H | H | 101 | 0.43 Toluene:Ethanol = 3:1 |
| 13a | H | $CH_2CH_2CN$ | 2,6-Di-Cl—$C_6H_3$ | H | $CH_2CH_2CN$ | 142 | 0.64 Toluene:Ethanol = 3:1 |
| b | H | H | 2,6-Di-Cl—$C_6H_3$ | H | $CH_2CH_2COOH$ | Oil | 0.46 Toluene:Ethanol = 3:1 |
| c | H | H | 2,6-Di-Cl—$C_6H_3$ | H | H | 156 | 0.56 Toluene:Ethanol = 3:1 |
| 14a | H | $CH_2CH_2CN$ | 2-Naphthyl | H | $CH_2CH_2CN$ | 140 | 0.54 Toluene:Ethanol = 3:1 |
| b | H | H | 2-Naphthyl | H | $CH_2CH_2COOH$ | 134 | 0.7 Toluene:Ethanol = 3:1 |
| c | H | H | 2-Naphthyl | H | H | 137 | 0.55 Toluene:Ethanol = 3:1 |
| 15a | H | $CH_2CH_2CN$ | 2-Thienyl | H | $CH_2CH_2CN$ | 104 | 0.3 Toluene:Ethanol = 3:1 |
| b | H | H | 2-Thienyl | H | $CH_2CH_2COOH$ | 113 | 0.33 Toluene:Ethanol = 3:1 |
| c | H | H | 2-Thienyl | H | H | 115 | 0.31 Toluene:Ethanol = 3:1 |
| 16a | H | $CH_2CH_2CN$ | 2,3,4-Tri-Cl—$C_6H_2$ | H | $CH_2CH_2CN$ | 174 | 0.64 Toluene:Ethanol = 3:1 |
| b | H | H | 2,3,4-Tri-Cl—$C_6H_2$ | H | $CH_2CH_2COOH$ | Oil | 0.61 Toluene:Ethanol = 3:1 |
| c | H | H | 2,3,4-Tri-Cl—$C_6H_2$ | H | H | 135 | 0.49 Toluene:Ethanol = 3:1 |
| 17a | 5-$OCH_3$ | $CH_2CH_2CN$ | $C_6H_5$ | H | $CH_2CH_2CN$ | Oil | 0.44 Toluene:Ethanol = 9:1 |
| b | 5-$OCH_3$ | H | $C_6H_5$ | H | $CH_2CH_2COOH$ | Oil | 0.5 Toluene:Ethanol = 9:1 |
| c | 5-$OCH_3$ | H | $C_6H_5$ | H | H | >225 | 0.51 $CH_2O_2$:Methanol = 9:1 |
| 18a | 5-$OCH_2Ph$ | $CH_2CH_2CN$ | $C_6H_5$ | H | $CH_2CH_2CN$ | Oil | 0.31 Toluene:Ethanol = 9:1 |
| b | 5-$OCH_2Ph$ | $CH_2CH_2CN$ | $C_6H_5$ | H | $CH_2CH_2CN$ | Oil | 0.35 Toluene:Ethanol = 9:1 |
| c | 5-$OCH_2Ph$ | H | $C_6H_5$ | H | $CH_2CH_2COOH$ | 60–62 | 0.33 Toluene:Ethanol = 9:1 |

-continued

Structure header: Indole with R¹ on benzene ring, N-Z on nitrogen, R⁴ on 3-position, and CH₂—CH₂—N(R²)—SO₂—R³ substituent.

| Example No. | R¹ | R² | R³ | R⁴ | Z | Melting point (°C.) | Rf value in |
|---|---|---|---|---|---|---|---|
| 19a | 5-CH₃ | H | C₆H₅ | H | H | Oil | 0.81 CH₂Cl₂:Methanol = 9:1 |
| b | 5-CH₃ | CH₂CH₂CN | C₆H₅ | H | CH₂CH₂COONa | Oil | 0.63 Toluene:Ethanol = 3:1 |
| c | 5-CH₃ | H | C₆H₅ | H | CH₂CH₂COOH | 205–215 | 0.25 CH₂Cl₂:Methanol = 9,5:5 |
| 20a | H | H | 4-H₅C₆—O—C₆H₄ | H | H | 147 | 0.5 Toluene:Ethanol = 3:1 |
| b | H | CH₂CH₂CN | 4-H₅C₆—O—C₆H₄ | H | CH₂CH₂CN | Oil | 0.67 Toluene:Ethanol = 3:1 |
| c | H | H | 4-H₅C₆—O—C₆H₄ | H | CH₂CH₂COOH | 110 | 0.26 Toluene:Ethanol = 3:1 |
| 21a | H | H | 3-Pyridyl | H | H | 110 | 0.92 CHCl₃:Methanol = 10:1 |
| 21b | H | CH₂CH₂CN | 3-Pyridyl | H | CH₂CH₂CN | 110 | 0.56 CHCl₃:Methanol = 10:1 |
| 21c | H | H | 3-Pyridyl | H | CH₂CH₂COOH | 112 | 0.29 CHCl₃:Methanol = 10:1 |
| 22a | H | H | 2-HO—3,5-Di-CH₃—C₆H₂ | H | H | 86–91 | 0.34 Toluene:Ethanol = 3:1 |
| 22b | H | CH₂CH₂CN | 2-HO—3,5-Di-CH₃—C₆H₅ | H | CH₂CH₂CN | Oil | 0.52 Toluene:Ethanol = 3:1 |
| 22c | H | H | 2-HO—3,5-Di-CH₃—C₆H₅ | H | CH₂CH₂COOH·NEt₃ | 150–154 | 0.41 Toluene:Ethanol = 3:1 |
| 23a | H | H | 8-Chinolyl | H | H | 140 | 0.38 CHCl₃:Methanol = 10:1 |
| 23b | H | CH₂CH₂CN | 8-Chinolyl | H | CH₂CH₂CN | Oil | 0.74 CHCl₃:Methanol = 10:1 |
| 23c | H | H | 8-Chinolyl | H | CH₂CH₂COOH | 130 | 0.62 CHCl₃:Methanol = 10:1 |
| 24a | H | H | 4(H₃C)₃C—C₆H₄ | H | H | 151 | 0.53 Toluene:Ethanol = 3:1 |
| 24b | H | CH₂CH₂CN | 4(H₃C)₃C—C₆H₄ | H | CH₂CH₂CN | Oil | 0.68 Toluene:Ethanol = 3:1 |
| 24c | H | H | 4(H₃C)₃C—C₆H₄ | H | CH₂CH₂COOH | 132 | 0.41 Toluene:Ethanol = 3:1 |
| 25a | H | H | 4-C₆H₅—C₆H₄ | H | H | 184 | 0.53 Toluene:Ethanol = 3:1 |
| 25b | H | CH₂CH₂CN | 4-C₆H₅—C₆H₄ | H | CH₂CH₂CN | 122 | 0.31 Toluene:Ethyl acetate = 3:1 |
| 25c | H | H | 4-C₆H₅—C₆H₄ | H | CH₂CH₂COOH | 164 | 0.44 Toluene:Ethanol = 3:1 |
| 26a | H | H | 4HOOC—CH=CH—C₆H₄ | H | H | 244 | 0.25 Toluene:Ethanol = 3:1 |
| 26b | H | CH₂CH₂CN | 4HOOC—CH=CH—C₆H₄ | H | CH₂CH₂CN | 138 | 0.78 Toluene:Ethanol = 3:1 |
| 26c | H | H | 4HOOC—CH=CH—C₆H₄ | H | CH₂CH₂COOH | 109 | 0.29 Toluene:Ethyl acetate = 3:1 |
| 27a | H | H | CH₃ | H | H | 128 | 0.25 Toluene:Ethanol = 3:1 |
| 27b | H | CH₂CH₂CN | CH₃ | H | CH₂CH₂CN | 74 | 0.58 Toluene:Ethanol = 3:1 |
| 27c | H | H | CH₃ | H | CH₂CH₂COOH | Oil | 0.37 Toluene:Ethyl acetate = 3:1 |
| 28a | H | H | CH₂CH₃ | H | H | 110 | 0.44 Toluene:Ethanol = 10:1 |
| 28b | H | CH₂CH₂CN | CH₂CH₃ | H | CH₂CH₂CN | 111 | 0.51 Toluene:Ethanol = 10:1 |
| 28c | H | H | CH₂CH₃ | H | CH₂CH₂COOH | 95 | 0.34 Toluene:Ethanol = 6:1 |
| 29a | H | CH₃ | C₆H₅ | CH₃ | H | 143 | 0.64 Toluene:Ethanol = 3:1 |
| 29b | H | CH₃ | C₆H₅ | CH₃ | CH₂CH₂CN | 98 | 0.21 Toluene:Ethyl acetate = 3:1 |
| 29c | H | CH₃ | C₆H₅ | CH₃ | CH₂CH₂COOH | 119 | 0.57 CH₂Cl₂:Methanol = 3:1 |
| 30a | H | H | 4-H₃C—C₆H₅ | H | H | 202 | 0.48 Toluene:Ethanol = 3:1 |
| 30b | H | CH₂CH₂CN | 4-H₃C—C₆H₅ | H | CH₂CH₂COOH·NEt₃ | Oil | 0.5 Toluene:Ethanol = 3:1 |
| 31a | H | H | 1-H₃C—Indol-2-on-5-yl | H | H | | |
| 31b | H | CH₂CH₂CN | 1-H₃C—Indol-2-on-5-yl | H | CH₂CH₂CN | | |
| 31c | H | H | 1-H₃C—Indol-2-on-5-yl | H | CH₂CH₂COOH | 155 | 0.5 Toluene:Ethanol = 3:1 |
| 32a | H | H | Benzothiadiazol-4-yl | H | H | Oil | 0.6 Toluene:Ethanol = 3:1 |
| 32b | H | CH₂CH₂CN | Benzothiadiazol-4-yl | H | CH₂CH₂CN | | |
| 32c | H | H | 2,3-Di-H₂N—C₆H₃ | H | CH₂CH₂COOH·NEt₃ | 121–7 | |
| 33a | H | H | 4-H₅C₂—C₆H₅ | CH₃ | H | 111 | 0.63 Toluene:Ethanol = 3:1 |

-continued

![Structure: indole with R1 on benzene ring, N-N at position 1, R4 at position 2, and CH2-CH2-N(R2)-SO2-R3 at position 3]

| Example No. | R¹ | R² | R³ | R⁴ | Z | Melting point (°C.) | Rf value in |
|---|---|---|---|---|---|---|---|
| 33b | H | CH₂CH₂CN | 4-H₅C₂—C₆H₅ | CH₃ | CH₂CH₂CN | 106 | 0,29 Toluene:Ethyl acetate = 3:1 |
| 33c | H | H | 4-H₅C₂—C₆H₅ | CH₃ | CH₂CH₂COOH | | |
| 34a | H | CH₂CH₂CN | 2-Thienyl | CH₃ | H | 127 | 0,54 Toluene:Ethyl acetate = 3:1 |
| 34b | H | H | 2-Thienyl | CH₃ | CH₂CH₂CN | 139 | 0,24 Toluene:Ethyl acetate = 3:1 |
| 34c | H | H | 2-Thienyl | CH₃ | CH₂CH₂COOH·NEt₃ | 122 | 0,57 CHCl₃:Methanol = 3:1 |
| 35a | H | H | 4-H₃C—C₆H₄ | COCH₃ | H | 167 | 0,2 Toluene:Ethyl acetate = 3:1 |
| 35b | H | H | 4-H₃C—C₆H₄ | COCH₃ | CH₂CH₂CN | 146 | 0,21 Toluene:Ethyl acetate = 3:1 |
| 35c | H | H | 4-H₃C—C₆H₄ | COCH₃ | CH₂CH₂COOH | | |
| 36a | H | H | 4-Cl—C₆H₄ | CH₃ | H | 133 | 0,63 Toluene:Ethanol = 3:1 |
| 36b | H | H | 4-Cl—C₆H₄ | CH₃ | CH₂CH₂CN | 112 | 0,24 Toluene:Ethyl acetate = 3:1 |
| 36c | H | H | 4-Cl—C₆H₄ | CH₃ | CH₂CH₂COOH·NEt₃ | 123 | 0,6 CHCl₃:Methanol = 3:1 |
| 37a | H | CH₂CH(CH₃)CN | 4-Cl—C₆H₄ | CH₃ | H | 99 | 0,44 Toluene:Ethanol = 10:1 |
| 37b | H | H | 4-Cl—C₆H₄ | H | CH₂CH(CH₃)COOH | | 0,41 Toluene:Ethanol = 3:1 |
| 38a | H | CH₂CH(CH₃)CN | 4-Cl—C₆H₄ | CH₃ | CH₂CH(CH₃)CN | Oil | 0,47 Toluol:Aceton = 4:1 |
| 38b | H | H | 4-Cl—C₆H₄ | CH₃ | H | 118 | 0,44 Toluene:Ethyl acetate = 3:1 |
| 39a | H | CH₂CH₂CN | 4-n-H₇C₃—C₆H₄ | CH₃ | CH₂CH₂CN | 112 | 0,28 Toluene:Ethyl acetate = 3:1 |
| 39b | H | H | 4-n-H₇C₃—C₆H₄ | CH₃ | H | | 0,28 Toluene:Ethanol = 3:1 |
| 39c | H | H | 4-n-H₇C₃—C₆H₄ | CH₃ | CH₂CH₂COOH | 132 | 0,65 Toluene:Ethanol = 3:1 |
| 40a | H | CH₂CH₂CN | 4-F—C₆H₄ | CH₃ | H | 87 | 0,27 Toluene:Ethyl acetate = 3:1 |
| 40b | H | H | 4-F—C₆H₄ | CH₃ | CH₂CH₂CN | 111 | 0,51 CHCl₃:Methanol = 3:1 |
| 40c | H | H | 4-F—C₆H₄ | CH₃ | CH₂CH₂COOH | 148 | 0,09 Toluene:Ethyl acetate = 3:1 |
| 41a | H | CH₂CH₂CN | 4-H₃C—C₆H₄ | CH(OH)CH₃ | H | | |
| 41b | H | H | 4-H₃C—C₆H₄ | CH(OH)CH₃ | CH₂CH₂CN | | |
| 41c | H | H | 4-H₃C—C₆H₄ | CH(OH)CH₃ | CH₂CH₂COOH | | |
| 42a | H | CH₂CH₂CN | C₆H₅ | CH(CH₃)₂ | H | | |
| 42b | H | H | C₆H₅ | CH(CH₃)₂ | CH₂CH₂CN | | |
| 42c | H | H | C₆H₅ | CH(CH₃)₂ | CH₂CH₂COOH | | |
| 43a | H | CH₂CH₂CN | 4-Cl—C₆H₄ | CH(CH₃)₂ | H | | |
| 43b | H | H | 4-Cl—C₆H₄ | CH(CH₃)₂ | CH₂CH₂CN | | |
| 43c | H | H | 4-Cl—C₆H₄ | CH(CH₃)₂ | CH₂CH₂COOH | | |
| 44a | H | CH₂CH₂CN | 4-F—C₆H₄ | CH(CH₃)₂ | H | | |
| 44b | H | H | 4-F—C₆H₄ | CH(CH₃)₂ | CH₂CH₂CN | | |
| 44c | H | H | 4-F—C₆H₄ | CH(CH₃)₂ | CH₂CH₂COOH | | |
| 45a | H | CH₂CH₂CN | C₆H₅ | C(CH₃)₃ | H | | |
| 45b | H | H | C₆H₅ | C(CH₃)₃ | CH₂CH₂CN | | |
| 45c | H | H | C₆H₅ | C(CH₃)₃ | CH₂CH₂COOH | | |
| 46a | H | CH₂CH₂CN | 4-Cl—C₆H₄ | C(CH₃)₃ | H | | |
| 46b | H | H | 4-Cl—C₆H₄ | C(CH₃)₃ | CH₂CH₂CN | | |
| 46c | H | H | 4-Cl—C₆H₄ | C(CH₃)₃ | CH₂CH₂COOH | | |
| 47a | H | CH₂CH₂CN | 4-F—C₆H₄ | C(CH₃)₃ | H | | |
| 47b | H | H | 4-F—C₆H₄ | C(CH₃)₃ | CH₂CH₂CN | | |
| 47c | H | H | 4-F—C₆H₄ | C(CH₃)₃ | CH₂CH₂COOH | | |
| 48a | 5-F | H | 4-F—C₆H₄ | CH₃ | H | 162-163 | 0,32 Toluene:Ethyl acetate = 8:2 |

-continued

Structure:

$$\text{R}^1\text{-substituted benzene fused to } N-Z \text{ ring with } CH_2-C(R^4)= \text{ and side chain } CH_2-CH_2-N(R^2)-SO_2-R^3$$

| Example No. | $R^1$ | $R^2$ | $R^3$ | $R^4$ | Z | Melting point (°C.) | Rf value in |
|---|---|---|---|---|---|---|---|
| 48b | 5-F | $CH_2CH_2CN$ | $4\text{-F}-C_6H_5$ | $CH_3$ | $CH_2CH_2CN$ | Oil | 0.25 Toluene:Ethyl acetate = 8:2 |
| 48c | 5-F | H | $4\text{-F}-C_6H_5$ | $CH_3$ | $CH_2CH_2COOH$ | 169–172 | 0.5 $CH_2Cl_2$:Methanol = 9:1 |
| 49a | 6-F | H | $4\text{-F}-C_6H_5$ | $CH_3$ | H | 142–143 | 0.42 Toluene:Ethyl acetate = 8:2 |
| 49b | 6-F | $CH_2CH_2CN$ | $4\text{-F}-C_6H_5$ | $CH_3$ | $CHCH_2CN$ | Oil | 0.29 Toluene:Ethyl acetate = 8:2 |
| 49c | 6-F | H | $4\text{-F}-C_6H_5$ | $CH_3$ | $CH_2CH_2COOH$ | Oil | 0.47 $CH_2Cl_2$:Methanol = 9:1 |
| 50a | 4-F | H | $4\text{-F}-C_6H_5$ | $CH_3$ | H | 155–156 | 0.42 Toluene:Ethyl acetate = 8:2 |
| 50b | 4-F | $CH_2CH_2CN$ | $4\text{-F}-C_6H_5$ | $CH_3$ | $CHCH_2CN$ | Oil | 0.34 Toluene:Ethyl acetate = 8:2 |
| 50c | 4-F | H | $4\text{-F}-C_6H_5$ | $CH_3$ | $CH_2CH_2COOH$ | Oil | 0.37 $CH_2Cl_2$:Methanol = 9:1 |
| 51a | 7-F | $CH_2CH_2CN$ | $4\text{-F}-C_6H_5$ | $CH_3$ | H | Oil | 0.32 Toluene:Ethyl acetate = 8:2 |
| 51b | 7-F | H | $4\text{-F}-C_6H_5$ | $CH_3$ | $CH_2CH_2CN$ | Oil | 0.25 Toluene:Ethyl acetate = 8:2 |
| 51c | 7-F | H | $4\text{-F}-C_6H_5$ | $CH_3$ | $CH_2CH_2COOH$ | Oil | 0.72 $CH_2Cl_2$:Methanol = 9:1 |
| 52a | 5-$OCH_3$ | $CH_2CH_2CN$ | $4\text{-F}-C_6H_5$ | $CH_3$ | H | Oil | 0.3 Toluene:Ethyl acetate = 8:2 |
| 52b | 5-$OCH_3$ | H | $4\text{-F}-C_6H_5$ | $CH_3$ | $CH_2CH_2CN$ | Oil | 0.18 Toluene:Ethyl acetate = 8:2 |
| 52c | 5-$OCH_3$ | H | $4\text{-F}-C_6H_5$ | $CH_3$ | $CH_2CH_2COOH$ | Oil | 0.45 $CH_2Cl_2$:Methanol = 9:1 |
| 53a | 4-$CH_3$ | $CH_2CH_2CN$ | $4\text{-F}-C_6H_5$ | $CH_3$ | H | Oil | 0.4 Toluene:Ethyl acetate = 8:2 |
| 53b | 4-$CH_3$ | H | $4\text{-F}-C_6H_5$ | $CH_3$ | $CH_2CH_2CN$ | Oil | 0.24 Toluene:Ethyl acetate = 8:2 |
| 53c | 4-$CH_3$ | H | $4\text{-F}-C_6H_5$ | $CH_3$ | $CH_2CH_2COOH$ | Oil | 0.62 $CH_2Cl_2$:Methanol = 9:1 |

USE EXAMPLE

Example 25

To determine the platelet aggregation-inhibiting action, blood from healthy volunteers of both sexes was used. 9 parts of blood were added to one part of 3.8% strength aqueous sodium citrate solution, as an anticoagulant. Platelet-rich citrated plasma (PRP) is obtained from this blood by means of centrifugation (Jürgens/-Beller, Klinische Methoden der Blutgerinnungsanalyse (Clinical methods of blood coagulation analysis); Thieme Verlag, Stuttgart 1959).

For these investigations, 0.8 ml of PRP and 0.1 ml of the active compound solution were preincubated at 37° C. in a waterbath. Platelet aggregation was then determined by the turbidometric method (Born, B. V. R., J. Physiol. (London), 162, 67, 1962) in an aggregometer at 37° C. (Therapeutische Berichte 47, 80–86, 1975). For this, 0.1 ml of collagen, an agent which induces aggregation, was added to the preincubated sample. The change in optical density in the sample of PRP was recorded over a period of 6 minutes and the deflection was determined after 6 minutes. The percentage inhibition in comparison with the control was calculated for this.

| N—Indolylethyl-sulphonic acid amide according to Example No. | Limit concentration for inhibition (mg/l) |
|---|---|
| 1c | 0.3–0.03 |
| 4b | 0.3–0.03 |
| 5b | 0.3–1.0 |
| 7c | 0.3–0.03 |
| 9c | 10–3 |
| 14c | 10–3 |
| 19c | 10–3 |

What is claimed is:

1. An N-Indolylethyl-sulphonic acid amide of the formula

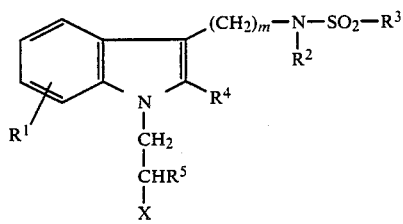

in which
R$^1$ is represented by A which denotes hydrogen, halogen, trifluoromethyl, carboxyl, C$_1$ to C$_8$-alkoxycarbonyl, the group $-S(O)_n-R^6$ in which
R$^6$ is C$_1$ to C$_8$-alkyl or C$_6$ to C$_{12}$-aryl and
n is one of the numbers, 0, 1 or 2,
or denotes the group

in which
R$^7$ and R$^8$ are each independently hydrogen, C$_1$ to C$_8$-alkyl, C$_6$ to C$_{12}$-aryl, C$_7$ to C$_{14}$-aralkyl or acetyl,
or represents the group $-O-R^9$ in which
R$^9$ is hydrogen, C$_1$ to C$_8$-alkyl, C$_6$ to C$_{12}$-aryl, C$_7$ to C$_{14}$-aralkyl, C$_1$ to C$_8$-SO$_2$-alkyl, C$_6$ to C$_{12}$-SO$_2$-aryl, C$_7$ to C$_{14}$-SO$_2$-aralkyl or trifluoromethyl,
or is C$_1$ to C$_8$-alkyl, C$_2$ to C$_8$-alkenyl or C$_5$ to C$_8$-cycloalkyl, optionally substituted by carboxyl, lower alkoxycarbonyl, halogen, hydroxyl, lower alkoxy and/or cyano,
R$^2$ is represented by B which denotes hydrogen, or is C$_1$ to C$_8$-alkyl or
C$_2$ to C$_8$-alkenyl or C$_5$ to C$_8$-cycloalkyl, optionally substituted by halogen, carboxyl, lower alkoxycarbonyl, carboxamide and/or cyano, R$^3$ is represented by C which denotes C$_1$ to C$_8$-alkyl, C$_2$ to C$_8$-alkenyl, C$_5$ to C$_8$-cycloalkyl, C$_6$ to C$_{12}$-aryl which is optionally substituted by halogen, cyano, trifluoromethyl, trifluoromethoxy, trifluoromethylthio, lower alkyl or lower alkenyl, which can themselves in turn be substituted by carboxyl or lower alkoxycarbonyl, lower alkoxy, carboxyl, hydroxyl, lower alkoxycarbonyl, phenyl, phenoxy, benzyloxy, benzylthio or the group

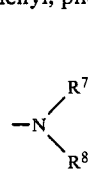

in which
R$^7$ and R$^8$ have the abovementioned meaning, or pyridyl, thienyl, furyl, pyrimidyl, piperazinyl, piperidinyl, morpholinyl, thiomorpholinyl, quinolyl, isoquinolyl, imidazolyl, triazolyl, tetrazolyl, thiadiazolyl, pyrrolyl, benzimidazolyl, benzothiadiazolyl, indolyl, indolonyl, thiazolyl, isothiazolyl, benzothiazolyl, benzoisothiazolyl or benzoisothiazolonyl, and is optionally substituted by lower alkyl, lower alkoxy, halogen, trifluoromethyl, trifluoromethoxy, amino, dimethylamino and/or acetylamino,
R$^4$ is represented by D which denotes hydrogen, C$_1$ to C$_8$-alkyl, C$_1$–C$_8$-hydroxyalkyl, C$_2$ to C$_8$-alkenyl, C$_5$–C$_8$-cycloalkyl, cyano, C$_6$ to C$_{12}$-aryl which is optionally substituted by halogen, methyl, methoxy or trifluoromethyl, C$_1$- to C$_8$-alkylcarbonyl or pyridyl, thienyl, furyl, pyrimidyl, imidazolyl or pyrrolyl, and is optionally substituted by lower alkyl, lower alkoxy, lower alkoxycarbonyl, carboxyl, halogen, trifluoromethyl, trifluoromethoxy, amino, dimethylamino or acetylamino,
R$^5$ is represented by E which denotes hydrogen or C$_1$- to C$_8$-alkyl,
X is represented by F which denotes carboxyl, C$_1$ to C$_8$-alkoxycarbonyl, cyano or carboxamido and
m is represented by G which denotes one of the numbers 2, 3 or 4, and salts thereof.

2. An N-Indolylethyl-sulphonic acid amide according to claim 1,
wherein
R$^1$ is represented by H which denotes hydrogen, fluorine, chlorine, bromine, trifluoromethyl, carboxyl, lower alkoxycarbonyl, the group —S(O)$_n$—R$^6$ in which
R$^6$ is lower alkyl or phenyl an
n is one of the numbers 0, 1 or 2,
the group

in which
R$^7$ and R$^8$ are each independently hydrogen, lower alkyl, phenyl, benzyl or acetyl,
or the group

—O—R$^9$ in which
R$^9$ is hydrogen, lower alkyl, phenyl, C$_7$ to C$_{10}$-aralkyl, —SO$_2$-lower alkyl, —SO$_2$-phenyl, —SO$_2$-benzyl or trifluoromethyl,
or lower alkyl, lower alkenyl, cyclopentyl or cyclohexyl, optionally substituted by identical or different substituents from the group consisting of carboxyl, lower alkoxycarbonyl, fluorine, chlorine, bromine and/or cyano,
R$^2$ is represented by I which denotes hydrogen, or lower alkyl, lower alkenyl, cyclopentyl or cyclohexyl, optionally substituted by fluorine, chlorine, bromine, carboxyl, lower alkoxycarbonyl and/or cyano,
R$^3$ is represented by J which denotes lower alkyl, lower alkenyl, cyclopentyl or cyclohexyl, phenyl or naphthyl which is optionally substituted by up to four substituents from the group consisting of fluorine, chlorine, bromine, cyano, hydroxyl, trifluoromethyl, trifluoromethoxy, lower alkyl or lower alkenyl, which can themselves in turn be substituted by carboxyl or C$_1$ to C$_4$-alkoxycarbonyl, lower alkoxy, carboxyl, C$_1$- to C$_4$-alkoxycarbonyl, benzyloxy, benzylthio phenyl, phenoxy and/or the group

in which
R$^7$ and R$^8$ have the abovementioned meaning, or pyridyl, thienyl, furyl, pyrimidyl, piperazinyl, pyperidinyl, morpholinyl, thiomorpholinyl, quinolyl, isoquinolyl, imidazolyl, triazolyl, tetrazolyl, thiadiazolyl pyrrolyl, benzimidazolyl, benzothiadiazolyl, indolyl, indolonyl, thiazolyl, isothiazolyl, benzothiazolyl, benzoisothiazolyl or benzoisothiazolonyl, optionally substituted by up to four substituents from the group consisting of fluorine, chlorine, bromine, amino, dimethylamino, acetylamino, trifluoromethyl, trifluoromethoxy, C$_1$ to C$_4$-alkyl and/or C$_1$ to C$_4$-alkoxy,
R$^4$ is represented by K which denotes hydrogen, lower alkyl, lower hydroxyalkyl, lower alkenyl, lower alkylcarbonyl, cyano, or phenyl, pyridyl, thienyl, furyl, pyrimidyl, imidazolyl or pyrrolyl optionally substituted by up to three substituents from the group consisting of fluorine, chlorine, methyl, methoxy and/or trifluoromethyl,
R$^5$ is represented by L which denotes hydrogen or lower alkyl,
X is represented by M which denotes carboxyl, lower alkoxycarbonyl or cyano and
m is represented by N which denotes one of the numbers 2 or 3,
and salts thereof.

3. An N-Indolylethyl-sulphonic acid amide according to claim 1,
wherein
R$^1$ is represented by O which denotes hydrogen, fluorine, chlorine, bromine, trifluoromethyl, the group —S(O)$_n$—R$^6$ in which
R$^6$ is methyl, ethyl or phenyl and
n is one of the numbers 0 or 2, amino, methylamino, dimethylamino, acetylamino, the group

—O—R$_9$ in which
R$^9$ is hydrogen, C$_1$ to C$_4$-alkyl, phenyl or benzyl, or C$_1$- to C$_4$-alkyl, optionally substituted by fluorine, chlorine and/or cyano,
R$^2$ is represented by P which denotes hydrogen, or C$_1$ to C$_4$-alkyl or C$_2$ to C$_4$-alkenyl, optionally substituted by carboxyl, C$_1$ to C$_4$-alkoxycarbonyl and/or cyano,
R$^3$ is represented by Q which denotes C$_1$- to C$_4$-alkyl, phenyl or naphthyl, optionally substituted by up to three substituents from the group consisting of fluorine, chlorine, bromine, cyano, hydroxyl, trifluoromethyl, carboxyvinyl, C$_1$ to C$_4$-alkyl, C$_1$- to C$_4$-alkoxy, C$_1$ to C$_4$-methyl- or ethoxycarbonylalkyl, phenyl, phenoxy, amino, dimethylamino and/or acetylamino, or pyridyl, thienyl, furyl, pyrimidyl, pyrazinyl, piperidinyl, morpholinyl or quinolyl, benzisothiazolonyl, benzothiazolyl or indolonyl, substituted by C$_1$–C$_4$-alkyl, fluorine, chlorine, amino or dimethylamino,
R$^4$ is represented by R which denotes hydrogen, methyl, ethyl, hydroxymethyl, hydroxyethyl, methylcarbonyl, cyano or phenyl,
R$^5$ is represented by S which denotes hydrogen or C$_1$- to C$_4$-alkyl,
X is represented by T which denotes carboxyl, C$_1$- to C$_4$-alkoxycarbonyl or cyano and
m is represented by U which denotes the number 2,
and salts thereof.

4. An N-indolylethyl sulphonic acid amide according to claim 1, wherein
R$^2$ is represented by V which denotes hydrogen and
X is represented by W which denotes carboxyl.

5. An N-indolylethyl sulfonic acid amide according to claims 1, 2, 3 or 4, in which the substituents R$^1$, R$^2$, R$^3$, R$^4$, R$^5$ and X and the index m are linked in the following manner:

| R$^1$ | R$^2$ | R$^3$ | R$^4$ | R$^5$ | X | m |
|---|---|---|---|---|---|---|
| A | B | C | D | L | F | G |
| O | P | Q | R | L | T | U |
| A | B | C | D | E | M | G |
| O | P | Q | R | S | M | U |
| A | B | C | D | E | F | N |
| O | P | Q | R | S | T | N |

| R¹ | R² | R³ | R⁴ | R⁵ | X | m |
|---|---|---|---|---|---|---|
| O | B | C | D | E | F | G |
| O | I | J | K | L | M | N |
| A | P | C | D | E | F | G |
| H | P | J | K | L | M | N |
| A | B | Q | D | E | F | G |
| H | I | Q | K | L | M | N |
| A | B | C | R | E | F | G |
| H | I | J | R | L | M | N |
| A | B | C | D | S | F | G |
| H | I | J | K | S | M | N |
| A | B | C | D | E | T | G |
| H | I | J | K | L | T | N |
| A | B | C | D | E | F | U |
| H | I | J | K | L | M | U |
| A | V | C | D | E | F | G |
| H | V | J | K | L | M | N |
| O | V | Q | R | S | T | U |
| A | B | C | D | E | W | G |
| H | I | J | K | L | W | N |
| O | P | Q | R | S | W | U |
| A | V | C | D | E | W | G |
| H | V | J | K | L | W | N |
| A | B | C | D | E | F | G |
| H | I | J | K | L | M | N |
| O | P | Q | R | S | T | U |
| A | I | J | K | L | M | N |
| A | P | Q | R | S | T | U |
| H | B | J | K | L | M | N |
| O | B | Q | R | S | T | U |
| H | I | C | K | L | M | N |
| O | P | C | R | S | T | U |
| H | I | J | D | L | M | N |
| O | P | Q | D | S | T | U |
| H | I | J | K | E | M | N |
| O | P | Q | R | E | T | U |
| H | I | J | K | L | F | N |
| O | P | Q | R | S | F | U |
| H | I | J | K | L | M | G |
| O | P | Q | R | S | T | G |
| H | B | J | K | L | M | N |
| H | P | Q | K | L | M | N |
| A | I | C | D | E | F | G |
| O | I | Q | R | S | T | U |
| H | B | C | D | E | F | G |
| H | P | Q | R | S | T | U |
| A | B | J | D | E | T | G |
| O | P | J | R | S | T | U |
| A | B | C | K | E | F | G |
| O | P | Q | K | S | T | U |

6. A medicament containing one or more 4-indolylethylsulphonic acid amides, according to claim 1 in an amount effective for combating thromboses, thromboembolisms, ischemias, allergies or asthmatic disorders and a pharmaceutically acceptable carrier.

7. A method of combating thromboses, thromboembolisms, ischemias, allergies or asthmatic disorders by administring an effective amount of a 4-indolylethyl-sulphonic acid amide according to claim 1.

* * * * *

UNITED STATES PATENT AND TRADEMARK OFFICE
CERTIFICATE OF CORRECTION

PATENT NO. : 4,774,240

DATED : September 27, 1988

INVENTOR(S) : Horst Böshagen et al

It is certified that error appears in the above-identified patent and that said Letters Patent is hereby corrected as shown below:

| | |
|---|---|
| Col. 2, line 55 | Correct spelling of --hydrogen-- |
| Col. 4, line 41 and Col. 5, line 36 | Correct spelling of --substituents-- |
| Col. 4, line 50 | Delete "methor" and substitute --meth-or-- |
| Col. 5, line 37 | Delete "x" and substitute --X-- |
| Col. 6, line 31 | Delete "$R^6$" and substitute --$R^5$-- |
| Col. 8, line 53 | Delete "Rhu 4" and substitute --$R^4$-- |
| Col. 8, line 60 | After "2 or 3" delete "or" and substitute --of-- |
| Col. 9, lines 44-45 | Correct --alkoxycarbonyls-- |
| Col. 10, line 46 | Correct spelling of --Solvents-- |
| Col. 12, line 1 | Correct --tryptamine-- |
| Col. 14, line 53 | Correct --Melting-- |
| Col. 22, Example No. 44c, under $R^3$ | Delete "4-F-$C_6H_5$" and substitute --4-F-$C_6H_4$-- |
| Col. 29, line 24 | Underneath "H V J K L W N" insert --O V Q R S W U-- |

Signed and Sealed this

Fifteenth Day of August, 1989

*Attest:*

DONALD J. QUIGG

*Attesting Officer*   *Commissioner of Patents and Trademarks*